United States Patent [19]
Seddon et al.

[11] Patent Number: 5,371,206
[45] Date of Patent: Dec. 6, 1994

[54] DNA ENCODING CHIMERIC FIBROBLAST GROWTH FACTORS

[75] Inventors: Andrew P. Seddon, Monroe; Peter Bohlen, Peekskill, both of N.Y.; Yakov Gluzman, Upper Saddle River, N.J.

[73] Assignee: American Cyanamid Company, Wayne, N.J.

[21] Appl. No.: 177,502

[22] Filed: Jan. 5, 1994

Related U.S. Application Data

[60] Division of Ser. No. 23,757, Feb. 26, 1993, Pat. No. 5,302,702, which is a continuation of Ser. No. 615,202, Nov. 23, 1990, abandoned.

[51] Int. Cl.$^5$ .................. C12V 15/01; C12V 15/18
[52] U.S. Cl. .................. 536/23.5; 536/23.51; 435/69.1; 435/69.4; 435/91.32; 435/172.1; 435/252.3; 435/252.33; 435/320.1; 530/399
[58] Field of Search ............... 536/23.5, 23.51; 435/69.1, 69.4, 91.32, 172.1, 252.3, 252.33, 320.1; 530/399

[56] References Cited

U.S. PATENT DOCUMENTS

| | | | |
|---|---|---|---|
| 4,518,584 | 5/1985 | Mark et al. | 424/85.2 |
| 4,588,585 | 5/1986 | Mark et al. | 424/85.2 |
| 4,959,314 | 9/1990 | Mark et al. | 424/85.5 |

OTHER PUBLICATIONS

Bollag et al., J. Mol. Biol., 218:493–494 (1991).
Seno et al., Biochem. Biophys. Res. Comm., 151(2):701–708 (1988).

*Primary Examiner*—Robert J. Hill, Jr.
*Assistant Examiner*—Shelly Guest Cermak
*Attorney, Agent, or Firm*—Estelle J. Tsevdos

[57] ABSTRACT

The present invention relates to novel chimeric fibroblast growth factors (FGF) wherein the alanine at amino acid 3 and serine 5 of native human recombinant basic fibroblast growth factor are replaced with glutamic acid. The N-terminus sequence of the present chimeric FGFs identify homology with that of human acidic fibroblast growth factor. The mitogenic properties of the native human recombinant basic FGF are exhibited by the present chimeric FGFs, and they are efficiently expressed in *E. coli* at significantly greater yields that previously reported. Novel variants of this new glu$^{3,5}$ basic fibroblast growth factor, such as those in which cysteine 78 and cysteine 96 are replaced, e.g., with serine or other amino acids, to produce stabilized versions of the glu$^{3,5}$ basic FGF and eliminate disulfide scrambled forms, are also described.

16 Claims, 6 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 465 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Pig     ( i x ) FEATURE:
        ( A ) NAME/KEY: CDS
        ( B ) LOCATION: 1..465

( x i ) SEQUENCE DESCRIPTION: SEQ ID NO:1:

```
ATG GCT GAA GGG GAA ATC ACC ACG CTG CCC GCC CTT CCG GAG GAT GGC        48
Met Ala Glu Gly Glu Ile Thr Thr Leu Pro Ala Leu Pro Glu Asp Gly
 1               5                  10                  15

GGC AGC GGC GCC TTC CCG CCC GGG CAC TTC AAG GAC CCC AAG CGG CTG        96
Gly Ser Gly Ala Phe Pro Pro Gly His Phe Lys Asp Pro Lys Arg Leu
                20                  25                  30

TAC TGC AAA AAC GGG GGC TTC TTC CTG CGC ATC CAC CCC GAC GGC CGA       144
```

|  |  |  |  |  |  |  |  |  |  |  |  |  |  |  |  |
|---|---|---|---|---|---|---|---|---|---|---|---|---|---|---|---|
| Tyr | Cys | Lys 35 | Asn | Gly | Gly | Phe | Phe 40 | Leu | Arg | Ile | His | Pro 45 | Asp | Gly | Arg |

| GTT | GAC | GGG | GTC | CGG | GAG | AAG | AGC | GAC | CCT | CAC | ATC | AAG | CTA | CAA | CTT | 192 |
|---|---|---|---|---|---|---|---|---|---|---|---|---|---|---|---|---|
| Val | Asp 50 | Gly | Val | Arg | Glu | Lys 55 | Ser | Asp | Pro | His | Ile 60 | Lys | Leu | Gln | Leu | |

| CAA | GCA | GAA | GAG | AGA | GGA | GTT | GTG | TCT | ATC | AAA | GGA | GTG | TGT | GCT | AAC | 240 |
|---|---|---|---|---|---|---|---|---|---|---|---|---|---|---|---|---|
| Gln 65 | Ala | Glu | Glu | Arg | Gly 70 | Val | Val | Ser | Ile | Lys 75 | Gly | Val | Cys | Ala | Asn 80 | |

| CGG | TAC | CTG | GCT | ATG | AAG | GAA | GAT | GGA | AGA | TTA | CTG | GCT | TCT | AAA | TGT | 288 |
|---|---|---|---|---|---|---|---|---|---|---|---|---|---|---|---|---|
| Arg | Tyr | Leu | Ala | Met 85 | Lys | Glu | Asp | Gly | Arg 90 | Leu | Leu | Ala | Ser | Lys 95 | Cys | |

| GTT | ACG | GAT | GAG | TGT | TTC | TTT | TTT | GAA | CGA | TTG | GAA | TCT | AAT | AAC | TAC | 336 |
|---|---|---|---|---|---|---|---|---|---|---|---|---|---|---|---|---|
| Val | Thr | Asp | Glu | Cys 100 | Phe | Phe | Phe | Glu | Arg 105 | Leu | Glu | Ser | Asn | Asn 110 | Tyr | |

| AAT | ACT | TAC | CGG | TCT | AGA | AAA | TAC | ACC | AGT | TGG | TAT | GTG | GCA | TTG | AAA | 384 |
|---|---|---|---|---|---|---|---|---|---|---|---|---|---|---|---|---|
| Asn | Thr | Tyr 115 | Arg | Ser | Arg | Lys | Tyr 120 | Thr | Ser | Trp | Tyr | Val 125 | Ala | Leu | Lys | |

| CGA | ACT | GGG | CAG | TAT | AAA | CTT | GGT | TCC | AAA | ACA | GGA | CCT | GGG | CAG | AAA | 432 |
|---|---|---|---|---|---|---|---|---|---|---|---|---|---|---|---|---|
| Arg | Thr 130 | Gly | Gln | Tyr | Lys | Leu 135 | Gly | Ser | Lys | Thr | Gly 140 | Pro | Gly | Gln | Lys | |

| GCT | ATA | CTT | TTT | CTT | CCA | ATG | TCT | GCT | AAG | AGC | | | | | | 465 |
|---|---|---|---|---|---|---|---|---|---|---|---|---|---|---|---|---|
| Ala 145 | Ile | Leu | Phe | Leu | Pro 150 | Met | Ser | Ala | Lys | Ser 155 | | | | | | |

( 2 ) INFORMATION FOR SEQ ID NO:2:

( i ) SEQUENCE CHARACTERISTICS:
        ( A ) LENGTH: 155 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

| Met 1 | Ala | Glu | Gly | Glu 5 | Ile | Thr | Thr | Leu | Pro 10 | Ala | Leu | Pro | Glu | Asp 15 | Gly |
|---|---|---|---|---|---|---|---|---|---|---|---|---|---|---|---|
| Gly | Ser | Gly | Ala 20 | Phe | Pro | Pro | Gly | His 25 | Phe | Lys | Asp | Pro | Lys 30 | Arg | Leu |
| Tyr | Cys | Lys 35 | Asn | Gly | Gly | Phe | Phe 40 | Leu | Arg | Ile | His | Pro 45 | Asp | Gly | Arg |
| Val | Asp 50 | Gly | Val | Arg | Glu | Lys 55 | Ser | Asp | Pro | His | Ile 60 | Lys | Leu | Gln | Leu |
| Gln 65 | Ala | Glu | Glu | Arg | Gly 70 | Val | Val | Ser | Ile | Lys 75 | Gly | Val | Cys | Ala | Asn 80 |
| Arg | Tyr | Leu | Ala | Met 85 | Lys | Glu | Asp | Gly | Arg 90 | Leu | Leu | Ala | Ser | Lys 95 | Cys |
| Val | Thr | Asp | Glu | Cys 100 | Phe | Phe | Phe | Glu | Arg 105 | Leu | Glu | Ser | Asn | Asn 110 | Tyr |
| Asn | Thr | Tyr 115 | Arg | Ser | Arg | Lys | Tyr 120 | Thr | Ser | Trp | Tyr | Val 125 | Ala | Leu | Lys |
| Arg | Thr 130 | Gly | Gln | Tyr | Lys | Leu 135 | Gly | Ser | Lys | Thr | Gly 140 | Pro | Gly | Gln | Lys |
| Ala 145 | Ile | Leu | Phe | Leu | Pro 150 | Met | Ser | Ala | Lys | Ser 155 | | | | | |

( 2 ) INFORMATION FOR SEQ ID NO:3:

( i ) SEQUENCE CHARACTERISTICS:
        ( A ) LENGTH: 465 base pairs
        ( B ) TYPE: nucleic acid
        ( C ) STRANDEDNESS: single
        ( D ) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Pig (ix) FEATURE:
    (A) NAME/KEY: CDS
    (B) LOCATION: 1..465

(xi) SEQUENCE DESCRIPTION: SEQ ID NO:3:

```
ATG GCT GAA GGG GAA ATC ACC ACG CTG CCC GCC CTT CCG GAG GAT GGC      48
Met Ala Glu Gly Glu Ile Thr Thr Leu Pro Ala Leu Pro Glu Asp Gly
 1               5                  10                  15

GGC AGC GGC GCC TTC CCG CCC GGG CAC TTC AAG GAC CCC AAG CGG CTG      96
Gly Ser Gly Ala Phe Pro Pro Gly His Phe Lys Asp Pro Lys Arg Leu
            20                  25                  30

TAC TGC AAA AAC GGG GGC TTC TTC CTG CGC ATC CAC CCC GAC GGC CGA     144
Tyr Cys Lys Asn Gly Gly Phe Phe Leu Arg Ile His Pro Asp Gly Arg
        35                  40                  45

GTT GAC GGG GTC CGG GAG AAG AGC GAC CCT CAC ATC AAG CTA CAA CTT     192
Val Asp Gly Val Arg Glu Lys Ser Asp Pro His Ile Lys Leu Gln Leu
50                  55                  60

CAA GCA GAA GAG AGA GGA GTT GTG TCT ATC AAA GGA GTG TCT GCT AAC     240
Gln Ala Glu Glu Arg Gly Val Val Ser Ile Lys Gly Val Ser Ala Asn
 65                  70                  75                  80

CGG TAC CTG GCT ATG AAG GAA GAT GGA AGA TTA CTG GCT TCT AAA TCT     288
Arg Tyr Leu Ala Met Lys Glu Asp Gly Arg Leu Leu Ala Ser Lys Ser
                 85                  90                  95

GTT ACG GAT GAG TGT TTC TTT TTT GAA CGA TTG GAA TCT AAT AAC TAC     336
Val Thr Asp Glu Cys Phe Phe Phe Glu Arg Leu Glu Ser Asn Asn Tyr
            100                 105                 110

AAT ACT TAC CGG TCT AGA AAA TAC ACC AGT TGG TAT GTG GCA TTG AAA     384
Asn Thr Tyr Arg Ser Arg Lys Tyr Thr Ser Trp Tyr Val Ala Leu Lys
        115                 120                 125

CGA ACT GGG CAG TAT AAA CTT GGT TCC AAA ACA GGA CCT GGG CAG AAA     432
Arg Thr Gly Gln Tyr Lys Leu Gly Ser Lys Thr Gly Pro Gly Gln Lys
    130                 135                 140

GCT ATA CTT TTT CTT CCA ATG TCT GCT AAG AGC                         465
Ala Ile Leu Phe Leu Pro Met Ser Ala Lys Ser
145                 150                 155
```

(2) INFORMATION FOR SEQ ID NO:4:

(i) SEQUENCE CHARACTERISTICS:
        (A) LENGTH: 155 amino acids
        (B) TYPE: amino acid
        (D) TOPOLOGY: linear     (ii) MOLECULE TYPE: protein     (xi) SEQUENCE DESCRIPTION: SEQ ID NO:4:

```
Met Ala Glu Gly Glu Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Ser Ala Asn
 65                  70                  75                  80
```

| | | | | | | | | | | | | | | |
|---|---|---|---|---|---|---|---|---|---|---|---|---|---|---|
| Arg | Tyr | Leu | Ala | Met | Lys | Glu | Asp | Gly | Arg | Leu | Leu | Ala | Ser | Lys | Ser |
| | | | | 85 | | | | 90 | | | | | 95 | |
| Val | Thr | Asp | Glu | Cys | Phe | Phe | Phe | Glu | Arg | Leu | Glu | Ser | Asn | Asn | Tyr |
| | | | 100 | | | | 105 | | | | | 110 | | |
| Asn | Thr | Tyr | Arg | Ser | Arg | Lys | Tyr | Thr | Ser | Trp | Tyr | Val | Ala | Leu | Lys |
| | | 115 | | | | 120 | | | | | 125 | | | |
| Arg | Thr | Gly | Gln | Tyr | Lys | Leu | Gly | Ser | Lys | Thr | Gly | Pro | Gly | Gln | Lys |
| | 130 | | | | 135 | | | | | 140 | | | | |
| Ala | Ile | Leu | Phe | Leu | Pro | Met | Ser | Ala | Lys | Ser | | | | |
| 145 | | | | | 150 | | | | | 155 | | | | |

( 2 ) INFORMATION FOR SEQ ID NO:5:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Human     ( x i ) SEQUENCE DESCRIPTION: SEQ ID NO:5:

AGCTTACCTG CCATGGCAGC CGGGAGCATC ACCACGCTGC CCGCCCTT    48

( 2 ) INFORMATION FOR SEQ ID NO:6:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: HUMAN     ( x i ) SEQUENCE DESCRIPTION: SEQ ID NO:6:

AGCTTCATAT GGCAGCCGGG AGCATCACCA CGCTGCCCGC CCTT    44

( 2 ) INFORMATION FOR SEQ ID NO:7:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: HUMAN     ( x i ) SEQUENCE DESCRIPTION: SEQ ID NO:7:

AGCTTCATAT GGCAGCCGGG AGCATCACCA CGCTGCCCGC CCTT    44

(2) INFORMATION FOR SEQ ID NO:8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(vi) ORIGINAL SOURCE:
        (A) ORGANISM: HUMAN     (xi) SEQUENCE DESCRIPTION: SEQ ID NO:8:

```
AGCTTCATAT GGCTGAAGGG GAAATCACCA CGCTGCCCGC CCTT                44
```

DNA ENCODING CHIMERIC FIBROBLAST GROWTH FACTORS

This is a division of copending application Ser. No. 08/023,757, filed on Feb. 26, 1993, now U.S. Pat. No. 5,302,702 which is a continuation of application Ser. No. 07/615,202, filed Nov. 23, 1990, abandoned.

BACKGROUND OF THE INVENTION

The present invention relates to novel chimeric basic fibroblast growth factors and to the enhanced production of such factors (bFGF).

Polypeptide growth factors are hormone-like modulators of cell proliferation and differentiation. Growth factors are responsible for the regulation of a variety of physiological processes, including development, regeneration and wound repair.

In the course of study of these factors, a number have been identified on the basis of the ability of extracts from various tissues, such as brain, pituitary and hypothalamus, to stimulate the mitosis of cultured cells. Numerous shorthand names have been applied to active factors in these extracts, including epidermal growth factor, platelet-derived growth factor, nerve growth factor, hematopoietic growth factor and fibroblast growth factor.

Fibroblast growth factor (FGF) was first described by Gospodarowicz in 1974 (Nature 249: 123-127) as derived from bovine brain or pituitary tissue which was mitogenic for fibroblasts and endothelial cells. It was later noted that the primary mitogen from brain was different from that isolated from pituitary. These two factors were named acidic and basic FGF, respectively, because they had similar if not identical biological activities but differed in their isoelectric points. Acidic and basic fibroblast growth factors (recently reviewed by Burgess, W. H., and Maciag, T. Ann. Rev. Biochem. 58: 575-606 (1989)) appear to be normal members of a family of heparin-binding growth factors that influence the general proliferation capacity of a majority of mesoderm- and neuroectoderm-derived cells (Gospodarowicz, D., et al., Nat. Cancer Inst. Mon. 48:109-130 (1978)), including endothelial cells, smooth muscle cells, adrenal cortex cells, prostatic and retina epithelial cells, oligodendrocytes, astrocytes, chrondocytes, myoblasts and osteoblasts (Burgess and Maciag, cited above at page 584). Although human melanocytes respond to the mitogenic influences of basic fibroblast growth factor but not acidic FGF most avian and mammalian cell types respond to both polypeptides (ibid.).

In addition to eliciting a mitogenic response that stimulates cell growth, fibroblast growth factors can stimulate a large number of cell types to respond in a non-mitogenic manner. These activities include promotion of cell migration into wound areas (chemotaxis), initiation of new blood vessel formation (angiogenesis), modulation of nerve regeneration (neurotropism), and stimulation or suppression of specific cellular protein expression, extracellular matrix production and cell survival important in the healing process (Burgess and Maciag, cited above, pages 584 to 588).

These properties, together with cell growth promoting action, provide a basis for using fibroblast growth factors in therapeutic approaches to accelerate wound healing and in prevention and therapeutic applications for thrombosis, artheriosclerosis, and the like. Thus, fibroblast growth factors have been suggested to promote the healing of tissue subjected to trauma (Davidson, J. M., et al. J. Cell Bio. 100:1219-1227 (1985)), to minimize myocardium damage in heart disease and surgery (U.S. Pat. Nos. 4,296,100 and 4,378,347 to Franco), and to increase neuronal survival and neurite extension (Walicke, P., et al., Proc. Nat. Acad. Sci. USA 83: 3012-3016 (1986)).

Complementary DNA clones encoding human acidic and human and bovine basic fibroblast growth factors have been isolated and sequenced, and the predicted amino acid sequences derived from the complementary DNAs agree with the structures determined by protein sequence analysis (summarized by Burgess and Maciag, cited above, at pages 580-581). The data predict acidic fibroblast growth factor (hereafter referred to as aFGF) to have 155 amino acids (ibid). The gene for basic fibroblast growth factor (hereafter referred to as bFGF) also codes for a 155 residue protein. For both aFGF and bFGF N-terminally truncated forms that exhibit full biologic activity including a 146-amino acid bFGF originally isolated and sequenced (Esch, F., et al, Proc. Nat. Acad. Sci. USA 82: 6507-6511 (1985)) and a 131-amino acid form. Analysis of the structures demonstrates a 55% identity between aFGF and bFGF (Burgess and Maciag, cited above at page 581).

Basic fibroblast growth factor may be extracted from mammalian tissue, but this requires several steps even when heparin-linked affinity chromatography is employed (U.S. Pat. Nos. 4,785,079 and 4,902,782 to Gospodarowicz, et al.), and the 146-amino acid species is generally obtained if extraction is done in the absence of protease inhibitors (ibid., column 9, lines 29 to 32). Bovine and human basic fibroblast growth factor cDNA have been expressed in *E. coli* (Iwane, M., et al., Biochem. Biophys. Res. Commun. 146:470-477 (1987) and Squires, C. H., et al., J. Biol. Chem. 263:16297-16302 (1988)) and *S. cervisiae* (Barr, P. J.. et al., J. Biol. Chem. 263: 16471-16478 (1988)). However, reported yields of product are low (see Eur. Pat. Ap. Pub. No. 228,449 to Esch, et al., page 18), and recombinant factors exhibit a marked tendency to undergo thiol-disulfide interchanges promoted by free thiol groups in the protein that result in the formation of disulfide scrambled species (Iwane, cited above).

A number of basic fibroblast growth factor analogues have been suggested. Muteins of bFGF having amino or carboxyl terminal amino acids deleted, amino acids added, cysteine substituted with a neutral amino acid such as serine, or aspartic acid, arginine, glycine, serine, or valine substituted with other acids have been suggested to have enhanced stability (Eur. Pat. Ap. Pub. No. 281,822 to Seno, et al., page 4, lines 1 to 3, and page 6, line 29 to page 7, line 19); the muteins comprise two or three additions, deletions or substitutions, with substitution of serine for cysteine the most preferred substitution (page 7, lines 18 to 23). Arakawa and Fox (Eur. Pat. Ap. Pub. No. 320,148) suggested replacing at least one, and more preferably two, of the cysteines found in natural bFGF with a different amino acid residue to yield a more stable analogue (page 4, lines 44 to 47); serine was illustrated in the Examples (page 13, lines 22 to 23), but alanine, aspartic acid and asparagine were also suggested (page 5, line 26 and page 13, line 25). Similarly, recombinant aFGFs having extraneous bond-forming cysteine replaced with serine, and oxidation-prone cysteine, methionine and tryptophan replaced with alanine, valine, leucine or isoleucine, to yield factors having enhanced or improved biological activity have also been suggested (Eur. Pat. Ap. Pub. No.

319,052 to Thomas Jnr and Linemeyer, page 17, lines 8 to 20).

A bFGF mutein lacking 7 to 46 amino acids from the carboxyl terminus and, optionally, having amino acids replacements was suggested to have improved stability while retaining activity in Eur. Pat. Ap. Pub. No. 326,907 to Seno, et al. (page 2, line 50 to page 3, line 4). Fiddes, et al, (Eur. Pat. Ap. Pub. No. 298723) suggested replacing basic or positively charged residues in the heparin binding domain encompassing residues 128 to 138 with neutral or negatively charged amino acids to produce forms of FGF having reduced heparin binding ability and enhanced potency (page 5, line 45, and page 5, line 54 to page 6, line 16). Bergonzoni, et al., suggested six analogues: 1) M1-bFGF, lacking residues 27 to 32; M2-bFGF, lacking residues 54 to 58; M3-bFGF, lacking residues 70 to 75; M4-bFGF, lacking residues 78 to 83; M5-bFGF, lacking residues 110 to 120; M5a-bFGF, having the position 128 lysine and the position 129 arginine replaced with glutamine residues; and M6b-bFGF, having the positions 119 and 128 lysines and the positions 118 and 129 arginines replaced by glutamine residues (Eur. Pat. Ap. Pub. No. 363,675, column 6, line 48 to column 7, line 13).

However, new stable and active forms of fibroblast growth factors are increasingly sought to use in the therapies indicated hereinabove.

SUMMARY OF INVENTION

The present invention relates to novel, full length (coding for 155 amino acid) human basic fibroblast growth factor genes and proteins which have the alanine residue at position 3 and the serine residue at position 5 of the native bFGF replaced with glutamic acid. $Glu^{3,5}hbFGF$ of this invention shares sequence identity with human acidic FGF at the N-terminal 8 amino acids and can thus be considered a chimeric FGF. More specifically, these factors are of human FGF but other mammalian species of FGFs are available through the present invention.

The $glu^{3,5}$ chimeric fibroblast growth factor has the mitogenic properties of tissue-derived bFGF, but expression in $E.\ coli$ is significantly greater than the native sequence. Thus, this invention provides novel, biologically active FGF and a method of preparing it in high yield.

The same finding exists with respect to novel variants of $glu^{3,5}hbFGF$. For example, a stabilized version of the growth factor is prepared by replacing cysteine 78 and, cysteine 96 with amino acids that eliminate thiol-disulfide interchange (disulfide scrambling), such as serine (SEQ ID #2). Thus, this invention not only modifies hbFGF (1-155) to significantly increase the yield of the factor expressed in $E.\ coli$, but also facilitates purification and enhances stability.

Therefore, this invention provides novel, biologically active fibroblast growth factors and methods of preparing these on a preparative scale. In a preferred embodiment, DNA encoding novel FGF of this invention is inserted into plasmids or vectors, which may be conveniently and efficiently conserved, stored or transported, if desired. The plasmids or vectors are then used to transform or transfect microorganism, e.g., $E.\ coli$, which likewise may be used to conserve, store, or transport, if desired, the genomic material encoding the novel FGF of this invention. Culture of these microorganisms under conditions that express the factors yield the polypeptides in abundance.

Since, as described above, growth factors released into traumatized areas accelerate the normal healing process, the novel fibroblast growth factors of this invention have therapeutic applications for healing burns, surgical incisions, and other wounds; for treating skin ulcers, including bedsores and the like; for cardiovascular conditions and restarting blood flow after heart attacks by revascularizing the damaged tissue; for enhancing bone repair and treating musculoskeletal injuries; and in neurodegenerative and other disease states.

DETAILED DESCRIPTION OF THE INVENTION

FIG. 1. Construction of $Glu^{3,5}, Ser^{78, 96}hbFGF$ cDNA. Using the expression plasmid pT7 $glu^{3,5}hbFGF$ prepared in Example 2 as a template, $cys^{78}$ to $ser^{78}$ and $cys^{96}$ to $ser^{96}$ mutations are directed using the following polymerase chain reaction mixtures: (1) T7 sense plus $ser^{78}$ antisense primers; and (2) T7 antisense plus ser sense primers. A polymerase chain reaction is then performed from (1) and (2) using T7 sense and T7 antisense primers as described in Example 3.

FIG. 2. Heparin HPLC of Natural hbFGF. Bound hbFGF (containing 154 amino acids) is eluted from a heparin sepharose column using a linear 0.6 to 3.0M NaCl gradient at 0.7 ml/min and monitored at 280 nm as described in Example 5.

FIG. 4. Reverse Phase HPLC of $Glu^{3,5}, Ser^{78,96}hbFGF$. A sample from heparin HPLC (8 $\mu g$) is loaded onto a 0.45×25 cm Vydac C4 column and eluted at 0.7 ml/min using a 0.1% trifluoroacetic acid/acetonitrile solvent system (0 to 28% acetonitrile in 15 min, 28 to 60% in 99 min, and 60 to 80% in 10 min) as described in Example 6.

FIG. 5. Bioassay Comparison of native bFGF with Recombinant bFGF's. The mitogenic activity of bFGF isolated from bovine brain is compared with human recombinant bFGF's on the proliferation of aortic arch bovine vascular endothelial cells as described in Example 7. Cells are grown in the presence of different amounts of bovine brain bFGF (10-155) (-▲-); natural sequence recombinant hbFGF (-●-); and $glu^{3,5}hbFGF$ (-o-) (determined by amino acids analysis) as indicated. After 4 days, acid phosphatase activity, equivalent to cell number over the cell density range examined, is determined at 405 nm.

FIG. 6. Bioassay Comparison of native bFGF with Chimeric bFGF's. The mitogenic activity of bovine brain bFGF (10-155) (-o-) and $glu^{3,5}, ser^{78,96}hbFGF$ (-●-) is compared using cells maintained in the presence of different amounts (determined by amino acids analysis) of growth factors as indicated for 5 days and cell number determined as described in Example 7.

DETAILED DESCRIPTION OF THE INVENTION

The present invention relates to the enhanced production and stabilization of new, basic fibroblast growth factors having about 155 amino acids. Although the human recombinant example provided herein, the FGF of the present invention is applicable to other mammalian species. A novel recombinant hbFGF of this invention is prepared by replacing alanine 3 and serine 5 with glutamic acid in full length human basic fibroblast growth factor. Glu$^{3, 5}$ hbFGF (SEQ ID #1) shares sequence identity with human aFGF at the N-terminal 8 amino acids and is thus considered a chimeric analogue of haFGF and hbFGF. This mutation significantly increases protein yield expressed in *Escherichia coli* as compared to native sequence bFGF.

Both recombinant native bFGF and glu$^{3, 5}$hbFGF exhibit microheterogeneity on heparin- and reverse phase- high performance liquid chromatography. While not wishing to be bound to any theory, this microheterogeneity appears to be due to thiol-disulfide interchange (disulfide scrambling) because it can be eliminated by treatment of the growth factors with a reducing agent prior to chromatography. Generation of a stabilized version of the growth factor and elimination of disulfide scrambled forms is accomplished by replacement of cysteine 78 and cysteine 96 with serine by site-directed mutagenesis.

A protein is defined herein as basic FGF if it shows FGF activity in in vitro and in vivo assays (summarized by Burgess and Maciag, cited above, pages 584 to 586); binds to heparin; and is eluted from heparin sepharose at 1.5–1.7M NaCl; and reacts immunologically with antibodies prepared using human or bovine basic FGF or synthetic or native peptides thereof, or to synthetic analogues of bFGF sequences conjugated to bovine serum albumin. A protein is defined herein as acidic FGF if it shows FGF activity in in vitro and in vivo assays; binds to heparin; and is eluted at 1.0–1.2M NaCl from heparin sepharose; and is immunologically reactive with antibodies prepared against human or bovine aFGF or against synthetic or native peptides thereof. A chimeric fibroblast growth factor shares the sequence of both types. Any type of mammalian fibroblast growth factor is encompassed by this invention, particularly human fibroblast growth factor.

The chimeric fibroblast growth factors of this invention include glu$^{3, 5}$hbFGF (SEQ ID #1) and glu$^{3, 5}$,ser$^{78, 96}$hbFGF (SEQ ID #2) having about 155 amino acids, and truncated forms having about 154 amino acids (e.g., those having no N-terminal methionine; see Example 6 (b)). This invention also encompasses glu$^{3, 5}$hbFGF analogues having the cysteine residues at positions 78 and 96 replaced with other amino acids, such as, for example alanine, glycine, arginine, tryptophan, lysine, aspartic acid, glutamic acid, asparagine, glutamine, histidine, isoleucine, leucine, valine, phenylalanine, tyrosine, methionine, serine, threonine or proline. Moreover, the FGF derivatives of this invention are not species specific, and include, for example, bovine FGF counterparts and others that share similar sequence homology with hbFGF.

The novel fibroblast growth factors of this invention may be prepared by assembling polypeptides from constituent amino acids, or from amino acids or peptides and polypeptides, using chemical or biochemical means known to those skilled in the art, such as, for example, by adding amino acids sequentially to shorter fibroblast forms at the N-terminus. Alternatively, the novel fibroblast growth factors of this invention may be prepared by recombinant protein synthesis involving preparation of DNA encoding chimeric FGF, insertion of the DNA into a vector, expression of the vector in host cells, and isolation of the recombinant FGF thereby produced.

DNA encoding the FGF of this invention may be prepared by altering a gene of human or bovine basic fibroblast growth factor by nucleotide deletions, nucleotide additions, or point mutations produced using standard means. An illustration is set out in Example 1. Because of the degeneracy of the genetic code, a variety of codon change combinations can be selected to form DNA that encodes the FGF of this invention, so that any nucleotide deletion(s), addition(s), or point mutation(s) that result in a DNA encoding chimeric FGF are encompassed by this invention. Since certain codons are more efficient for polypeptide expression in certain types of organisms, the selection of fibroblast gene alterations to yield DNA material that codes for the FGF of this invention are preferably those that yield the most efficient expression in the type of organism which is to serve as the host of the recombinant vector. Altered codon selection may also depend upon vector construction considerations.

Fibroblast growth factor DNA starting material which can be altered to form chimeric DNA may be natural, recombinant or synthetic. Thus, DNA starting material may be isolated from tissue or tissue culture, constructed from oligonucleotides using conventional methods, obtained commercially, or prepared by isolating RNA coding for bFGF from fibroblasts, using this RNA to synthesize single-stranded cDNA which can be used as a template to synthesize the corresponding double stranded DNA.

Illustrating the present invention are cloned complementary DNA sequences defining chimeric fibroblast polypeptide sequences such as that constructed in Examples 2 and 3. Also encompassed are DNA sequences homologous. or closely related to complementary DNA described herein, namely DNA sequences which hybridize, particularly under stringent conditions, to chimeric fibroblast cDNA, and RNA corresponding thereto. In addition to the chimeric FGF-encoding sequences, DNA encompassed by this invention may contain additional sequences, depending upon vector construction sequences, that facilitate expression of the gene.

DNA encoding the chimeric growth factors of this invention, or RNA corresponding thereto, are then inserted into a vector, e.g., a pBR, pUC, pUB or pET series plasmid, and the recombinant vector used to transform a microbial host organisms. Host organisms may be bacterial (e.g., *E. coli* or *B. subtilis*), yeast (e.g., *S. cervisiae*) or mammalian (e.g., mouse fibroblast). This invention thus also provides novel, biologically functional viral and circular plasmid RNA and DNA vectors incorporating RNA and DNA sequences describing the chimeric growth factors generated by standard means. Culture of host organisms stably transformed or transfected with such vectors under conditions facilitative of large scale expression of the exogenous, vectorborne DNA or RNA sequences and isolation of the desired polypeptides from the growth medium, cellular lysates, or cellular membrane fractions yields the desired products. An example of expression of hbFGF mutants in *E. coli* is given in Example 4.

The present invention provides for the total and/or partial manufacture of DNA sequences coding for glu$^{3, 5}$hbFGF, glu$^{3, 5}$,ser$^{78, 96}$hbFGF, and other glu$^{3, 5}$hbFGF having the cysteines at positions 78 and 96 replaced with other amino acids that eliminate disulfide scrambling, and including such advantageous characteristics as incorporation of codons preferred for expression by selected non-mammalian hosts, provision of sites of cleavage by restriction by endonuclease enzymes, and provision of additional initial, terminal or intermediate DNA sequences which facilitate construction of readily expressed vectors. Correspondingly, the present invention provides for manufacture (and development by site specific mutagenesis of cDNA and genomic DNA) of DNA sequences coding for microbial expression of chimeric fibroblast growth factor which differ from the forms specifically described herein in terms of identity or location of one or more amino acids residues (i.e., deletion analogues containing less than all of the residues specified for hbFGF, and/or substitution analogues wherein one or more residues are replaced by and/or addition analogues wherein one or more residues are added to a terminal or medial portion of the polypeptide), and which share the biological properties of $glu^{3,5}hbFGF$ and $glu^{3,5},ser^{78,96}hbFGF$.

DNA (and RNA) sequences of this invention code for all sequences useful in securing expression in procaryotic or eucaryotic host cells of polypeptide products having at least a part of the primary structural conformation, and one or more of the biological properties of chimeric fibroblast growth factor which are comprehended by: (a) the DNA sequenced encoding $glu^{3,5}hbFGF$ and $glu^{3,5},ser^{78,96}hbFGF$ as described herein, or complementary strands; (b) DNA sequences which hybridize (under hybridization conditions as described herein or more stringent conditions) to DNA sequences defined in (a) or fragments thereof; and (c) DNA sequences which, but for the degeneracy of the genetic code, would hybridize to the DNA sequenced defined in (a) and (b) above. Specifically comprehended are genomic DNA sequenced encoding allergic variant forms of chimeric fibroblast growth factors included therein, and sequences encoding chimeric fibroblast growth factor RNA, fragments thereof, and analogues wherein RNA or DNA sequenced may incorporate codon facilitating transcription or RNA replication of messenger RNA in non-vertebrate hosts.

Figure 2:
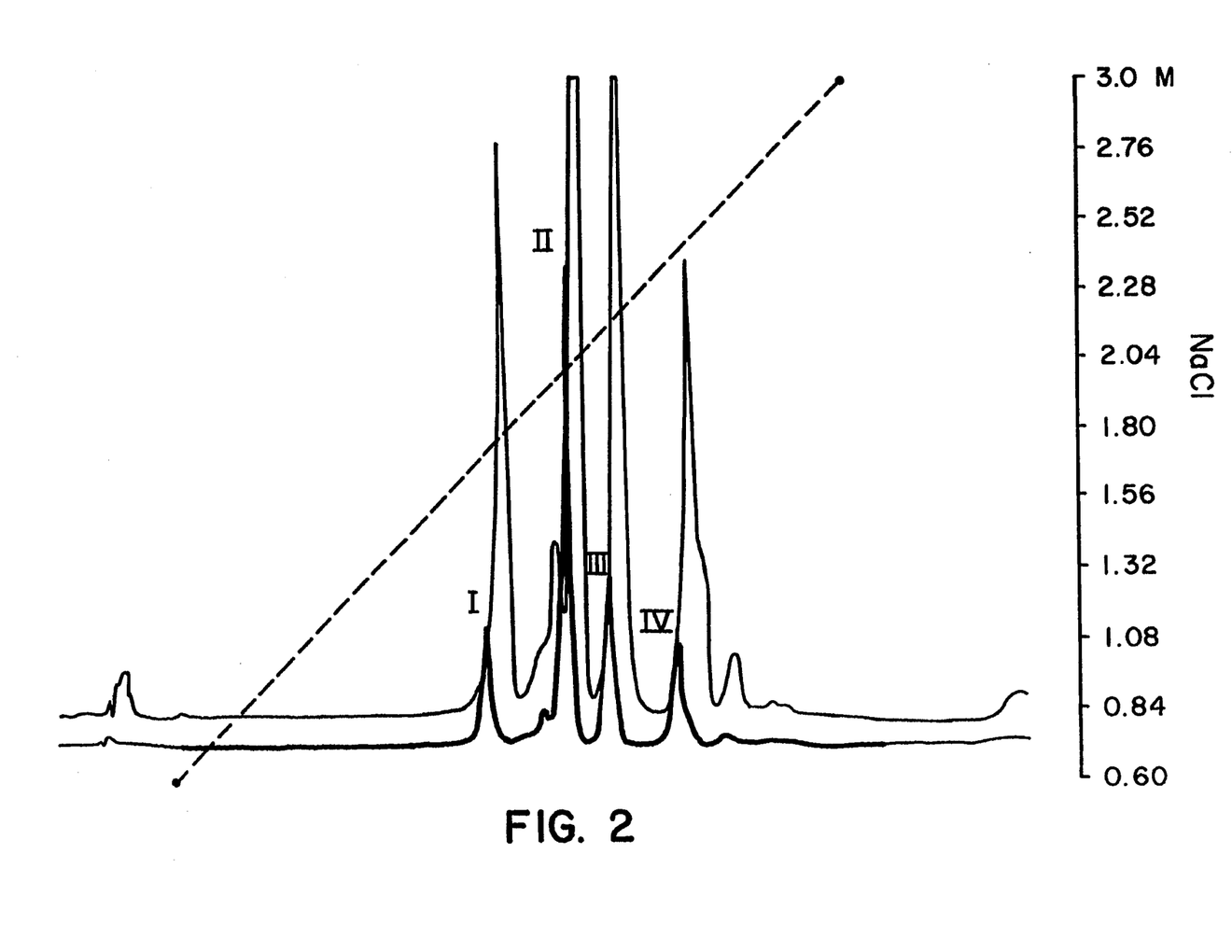
Figure 3:
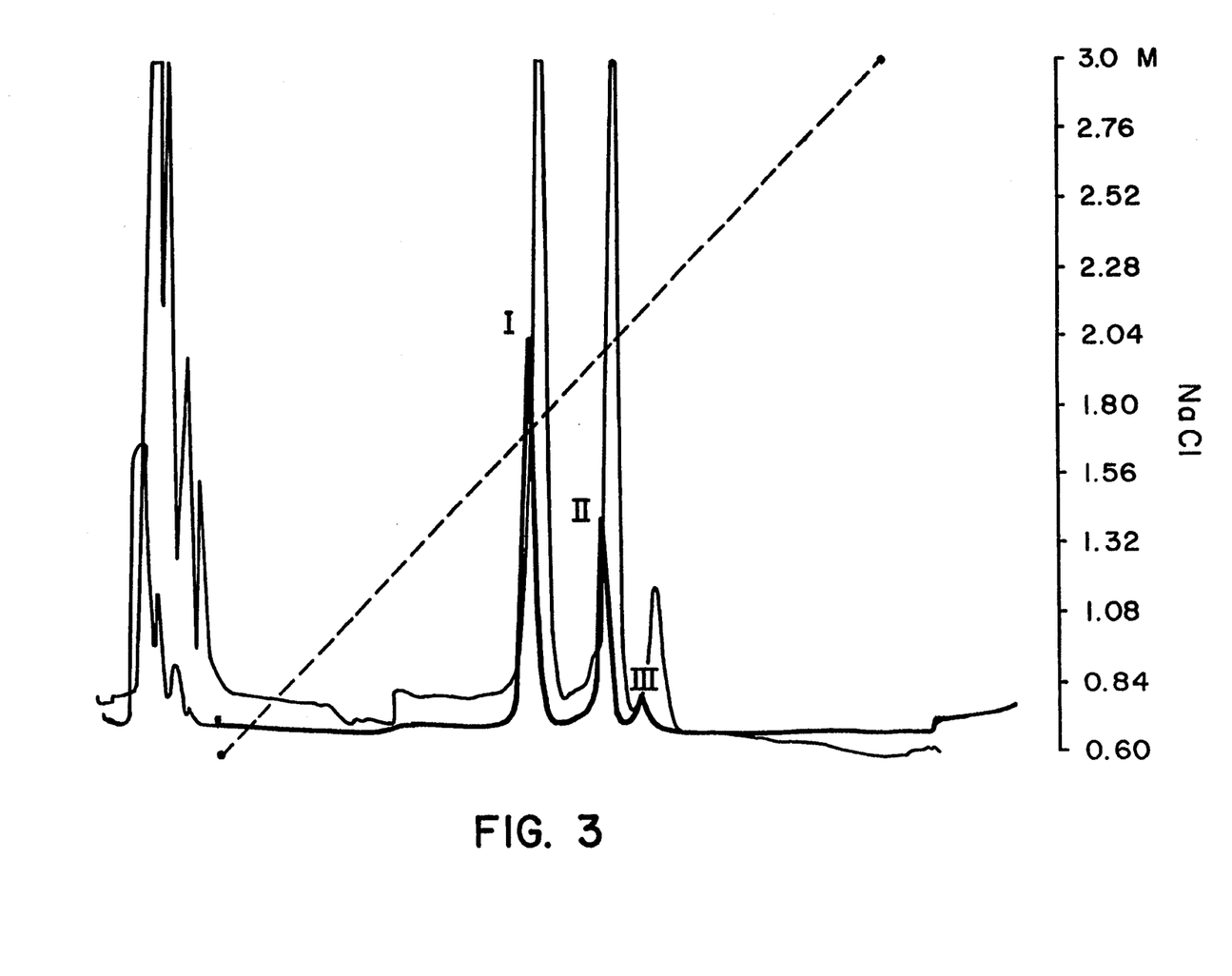
FIG. 3. Heparin HPLC of Reduced Recombinant hbFGF. An elution profile from heparin HPLC of a portion of pooled material from heparin sepharose chromatography that has been reduced with dithiotheitol as described in Example 6.

Isolation and purification of microbially expressed polypeptides provided by the invention may be by conventional means including, for example, preparative chromatographic separations such as that illustrated in FIGS. 2 and 3, and immunological separations, including monoclonal and/or polyclonal antibody preparations, i.e. example purification is given in Example 5.

As summarized above and described in detail in the Examples below, and example chimeric fibroblast growth factor of this invention is full length (155 amino acids) human recombinant basic fibroblast growth factor having alanine 3 and serine 5 replaced with glutamic acid expressed, using the T7 RNA polymerase expression system, in *E. coli*. (The numbering for bFGF adopted here is for the 155 amino acid form as described in Abraham et al, 1986 and refers to the methionine codon as position 1) Both recombinant native bFGF and $glu^{3,5}hbFGF$ exhibit extensive microheterogeneity on heparin- and RP-PHLC (FIG. 2) which is eliminated by treatment of the growth factor with a reducing agent such as dithiothreitol prior to chromatography (FIG. 3). Generation of a stabilized version of the growth factor and elimination of disulfide scrambled forms is accomplished by replacement of cysteine 78 and cysteine 96 with serine by site-directed mutagenesis (Example 3).

The yield of both $glu^{3,5}hbFGF$ and $glu^{3,5},ser^{78,96}hbFGF$ in this expression system like aFGF cDNA, is 10-fold higher than parental bFGF cDNA (Example 5). $Glu^{3,5}hbFGF$ and $glu^{3,5}ser^{78,96}hbFGF$ share sequence identity with haFGF at the N-terminal 8 amino acids. Thus, these derivatives are chimeric.

Figure 5:
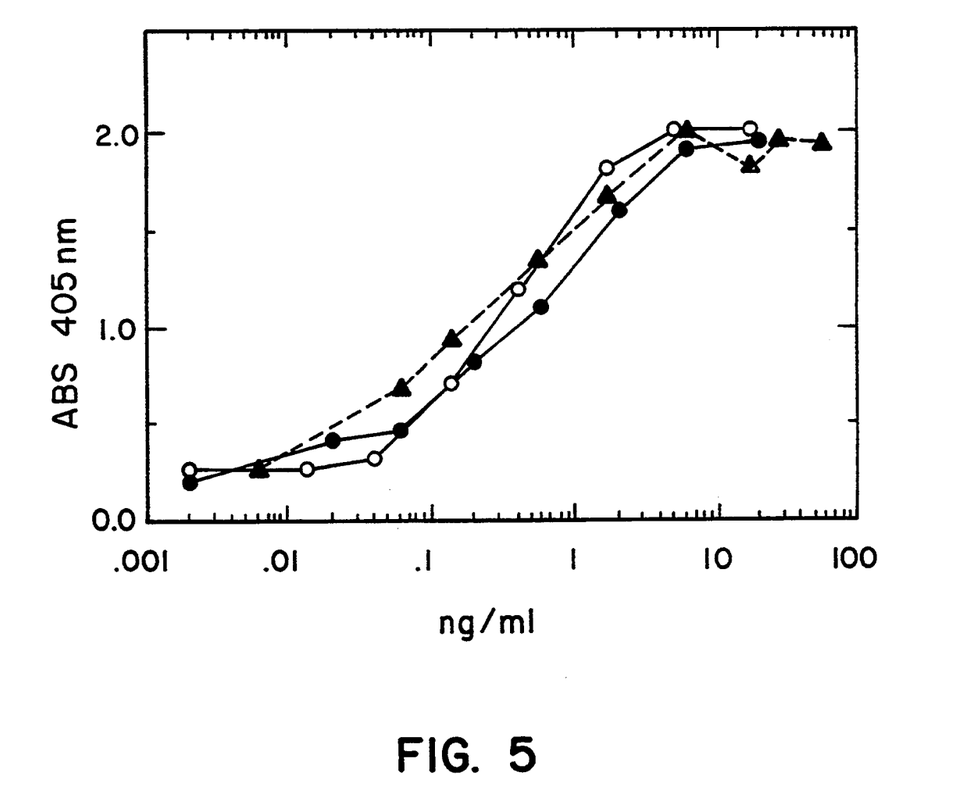
Figure 6:
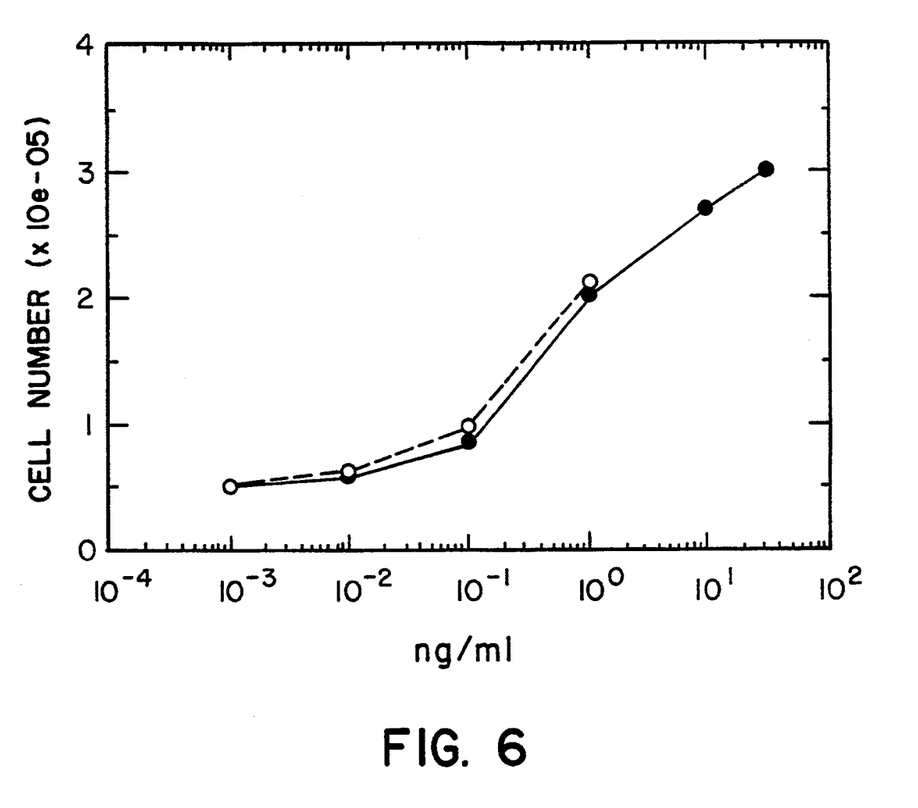

The polypeptides of this invention retain biological activity as fibroblast growth factors. For example when the mitogenic properties of recombinant hbFGF and mutant proteins are compared to bFGF (10-155) originally isolated from bovine brain (Example 7), human recombinant bFGF and $glu^{3,5}hbFGF$ show a dose-dependent stimulation of endothelial cell growth that was essentially identical to that for bovine brain bFGF (FIG. 5). Replacement of cysteine 78 and 96 with serine to give $glu^{3,5},ser^{78,96}hbFGF$ had no effect on the mitogenic potency and gave a dose-response curve that was indistinguishable from that determined for tissue-derived bovine bFGF (FIG. 6).

The modifications to hbFGF described herein significantly increase the yield of growth factor expressed, facilitate its purification, eliminates microheterogeniety due to disulfide scrambling, and enhances stability while retaining full biological activity.

EXAMPLES

The following examples are presented to further describe and explain the present invention and the characterization techniques employed, and should not be taken as limiting in any regard. Unless otherwise indicated, all parts and percentages are by weight, and are based on the weight at the particular stage of the processing being described.

EXAMPLE 1

Construction of an Expression Plasmid

A synthetic gene encoding the 155 amino acid form of human bFGF (Abraham, J. A., et al, EMBO J. 5: 2523–2528 (1986)) cloned into pUC 18 was purchased from British Bio-technology, Oxford, UK. Destruction of the internal NcoI restriction site at positions −2 to 3, which includes the N-terminal methionine codon of the bFGF cDNA, and introduction of a unique NdeI site is as follows. The nucleotide sequence (−12 to 36) to be changed (a, below) is excised from pUC 18 with HindIII and BspMII and a synthetic fragment (b, below) containing an internal NdeI site cloned into pUC 18. This cloning results in a construct that contains a 4 nucleotide deletion in the upstream non-coding region compared to the original construct (see below). This deletion has no effect on the relative protein yields of bFGF using the expression system described below.

5'
  AGCTTACCTGCCATGGCAGCCGGGAG-
  CATCACCACGCTGCCCGCCCTT 3'  (a)

5'
  AGCTTCATATGGCAGCCGGGAGCAT-
  CACCACGCTGCCCGCCCTT 3'  (b)

Only the sense strands are shown for the original (a) and modified (b) fragments, respectively. The codon underlined indicates the position of the methionine start codon.

The cDNA encoding bFGF is then excised from pUC 18 with NdeI and BamH1 and cloned into the NdeI and BamH1 sites of the expression vector pT7 Kan 5, derivative of pET-3a (plasmid for Expression by bacteriophage T7, as defined in Rosenberg, A., et al, Gene 56: 125–135 (1987) at page 128) containing the T7 promoter for RNA polymerase.

EXAMPLE 2

CONSTRUCTION OF GLU$^{3, 5}$ hbFGF

The protocol for the construction of glu $^{3, 5}$hbFGF is identical to that described above for the introduction of the NdeI restriction site except that the region encoding the first 5-terminal amino acids of basic FGF (c) are changed to encode those of acidic FGF (d):

5'
   AGCTTCATATGGCAGCCGGGAGCAT-
   CACCACGCTGCCCGCCCTT 3'    (c)

5'
   AGCTTCATATGGCTGAAGGGGAAAT-
   CACCACGCTGCCCGCCCTT 3'    (d)

Only the sense strands are shown for the original (c) and modified (d) fragments, respectively. The codons underlined indicate those changed to encode glutamic acid at positions 3 and 5.

EXAMPLE 3

Construction of Glu$^{3, 5}$Ser$^{78, 96}$hbFGF

The expression plasmid pT7 glu$^{3, 5}$hbFGF is used as a template for oligonucleotide site-directed mutagenesis. Two mutagenic oligonucleotide primers are designed to change cysteine codons at positions 78 and 96 to serine codons. The primer for serine at position 96 is to the sense strand (60-mer; 238-297) whereas that for serine at position 78 is to the anti-sense strand (30-mer; 251-222). In addition to these mutagenic primers, primers to the T7 promotor (nucleotide −12 to +13) and terminator regions (nucleotide −75 to −54) are designed (19).

Figure 1:
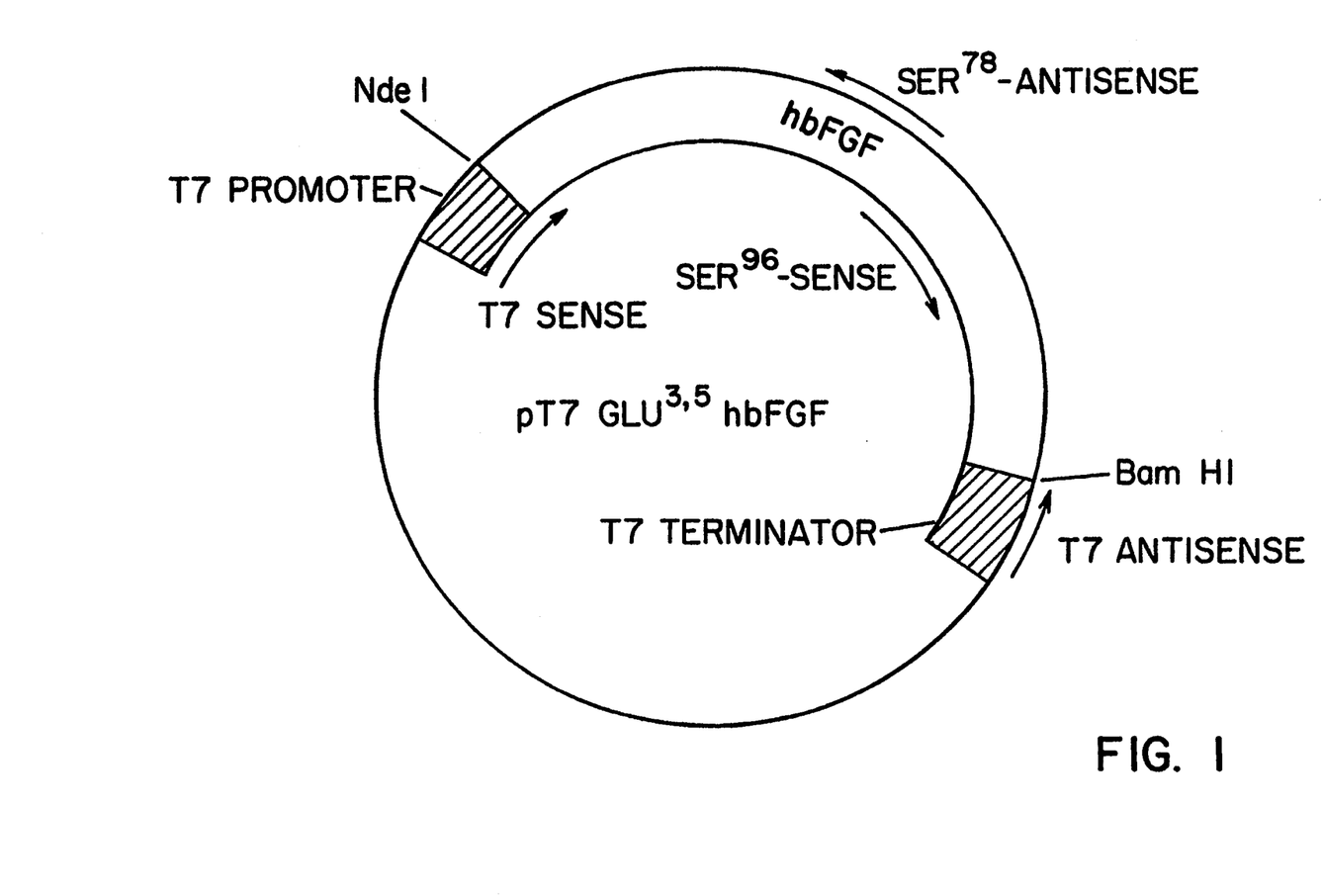

Mutation of the modified FGF gene is accomplished by use of a polymerase chain reaction (PCR). Two reaction mixtures containing HindIII cut plasmid DNA are prepared as shown schematically in FIG. 1: (i) T7 sense plus Ser 78 antisense primers to yield an expected 319 base pair product, and (ii) T7 antisense plus Ser 96 sense primers to produce an expected 294 basepair product. PCR mixtures are prepared according to the manufacturer's instructions (Perkin Elmer Cetus, Norwalk, Conn.). PCR is performed using Tag polymerase for 30 amplification cycles each 92° C. for 1 min, 50° C. for 5 sec, and 72° C. for 1 min, and the products analyzed by agarose gel electrophoresis.

Excess primers are separated from the amplified DNA fragments by 3 successive rounds of concentration and dialysis using 30,000 molecular weight Millipore microconcentrators. Portions of the retentates are combined and amplified using the PCR as described above except that the primers used correspond to the T7 promoter (sense) and T7 terminator (antisense) regions. See FIG. 1. The 599 basepair PCR product is then treated with NdeI and BamHI and purified by agarose gel electrophoresis. The purified fragment is then cloned into the T7 expression vector, pET-3a(M13), a derivative of pET-3a.

EXAMPLE 4

Expression of Natural Sequence hbFGF and hbFGF Mutants

Following sequence verification (Sanger, F., et al., Proc. Nat. Acad. Sci. 74:5463-5467 (1977)), the genes encoding the bFGF mutants are transformed into competent BL21 pLysS cells. *E. coli* cells harboring the plasmids are grown in Luria broth containing kanamycin sulfate (50 µg/ml or ampicillin (100 µg/ml) for plasmid glu$^{3, 5}$ser$^{78, 96}$hbFGF and chloramphenicol (34 µg/ml) at 37° C. to about 0.6 absorbance units at 600 nm. bFGF synthesis is induced by addition of isopropyl-beta-D-thiogalactopyranoside (1 mM). Two hours postinduction, the cells are then harvested by centrifugation at 4° C.

EXAMPLE 5

Purification of hbFGF Mutants

Cell pellets from 1 liter cultures are resuspended in 30 ml 50 mM Tris, 0.1 mM EDTA buffer, pH 7.6, and lysed by 3 rapid freeze/thaw cycles. The lysate is then treated with DNase I (20 µg/ml) in the presence of 5 mM MgC$_{12}$ for 20 min at 4° C. and centrifuged at 10,000×g for 20 min to remove cell debris. bFGF activity is found to be equally distributed in the pellet and supernatant fractions.

bFGF is purified from the supernatant solution by heparin-sepharose column chromatography as described by Gospodarowicz, D., et al., Proc. Nat. Acad. Sci. USA 81:6963-6967 (1984), and eluting with a linear salt gradient from 0.6 to 3.0M NaCl. The fractions containing growth factor are pooled and diluted with 10 mM, pH 7.6 Tris buffer to give a final NaCl concentration of about 0.6M.

This is loaded onto a 0.75×7.5 cm TSK Heparin-5PW column (TosoHaas, Philadelphia, Pa.) equilibrated with 10 mM, pH 7.6 Tris, 0.6M NaCl. Elution of bound material is monitored at 280 nm and is accomplished using a linear salt gradient (0.6 to 3.0M NaCl in 60 min) at a flow rate of 0.7 ml/min.

Using the T7 expression system described in Example 4, the yield of native sequence hbFGF (2-155) is about 0.8 mg/1 bacterial culture. With native sequence haFGF, a 6 to 8 mg/liter yield is obtained. Glu$^{3, 5}$hbFGF expressed in the same system gives 8 to 10 mg/liter of purified factor.

Large scale fermentation (10 L) of *E. coli* containing the plasmid pT7 glu$^{3, 5}$,ser$^{78, 96}$ gives about 1 mg of purified growth factor per g of cell paste. Protein yield of the chimeric ser$^{78, 96}$ variant and distribution of the protein in the supernatant and pellet fractions of the bacterial extract are similar to that observed for glu$^{3, 5}$hbFGF.

EXAMPLE 6

Characterization of hbFGF and hbFGF Mutants (a) Chromatographic Behavior

Heparin HPLC purified bFGF's are analyzed by reverse phase high performance liquid chromatography, RP-HPLC (C$_4$, Vydac, the separations Group, Hesperia, Calif.) using a 0.1% trifluoroacetic acid/acetonitrile gradient (0 to 28% CH$_3$CN in 15 min, 28–60% in 99 min, and 60 to 30% in 10 min) at a flow rate of 0.7 ml/min. Elution of bound material is monitored at 210 nm.

The elution profile from heparin sepharose chromatography of a crude cell homogenate containing native sequence hbFGF (2-155) shows two major protein peaks both of which possess mitogenic activity and contain a major protein species of M$_r$ 17,000 by sodium dodecyl sulfate polyacrylamide gel electrophoresis (SDS-PAGE). C$_4$ reverse phase-high performance liquid chromatorgaphy (RP-HPLC) of material from each of the two peaks obtained from the heparin sepharose step followed by N-terminal sequence analysis of the resolved components identify at least 3 distinct forms of bFGF.

As a first approach to analyze this apparent microheterogeneity, the contribution of thiol-disulfide interchange (disulfide scrambling) in the generation of chromatographically distinct species is assessed by treatment with a reducing agent. Incubation of a portion of heparin sepharose purified bFGF with dithiothreitol (2 mM) for 10 min at 37° C. followed by RP-HPLC analysis shows that the peaks previously identified as bFGF species chromatograph essentially as a single peak.

High resolution TSK Heparin HPLC of 2 protein peaks containing FGF from the heparin sepharose step reveals 4 major protein components that elute over a range of 1.6 to 2.3M NaCl (FIG. 2). Analysis by SDS-PAGE of these peaks shows P-I, P-III and P-IV to contain a single protein band that migrates with an $M_r$ of 17,000 consistent with that hbFGF(2-155), whereas PII exhibits an $M_r$ of about 22,000 and is identified by N-terminal sequence analysis as a contaminant. Treatment of a portion of the pooled material from heparin sepharose chromatography with dithiothreitol (5 mM) for 10 min at room temperature followed by heparin HPLC shows an increase in the amount of P-I, a reduction in that of P-III and the disappearance of P-IV; the position and intensity of P-II containing the $M_r$ 22,000 impurity is unaffected by this treatment (FIG. 3).

Figure 4:
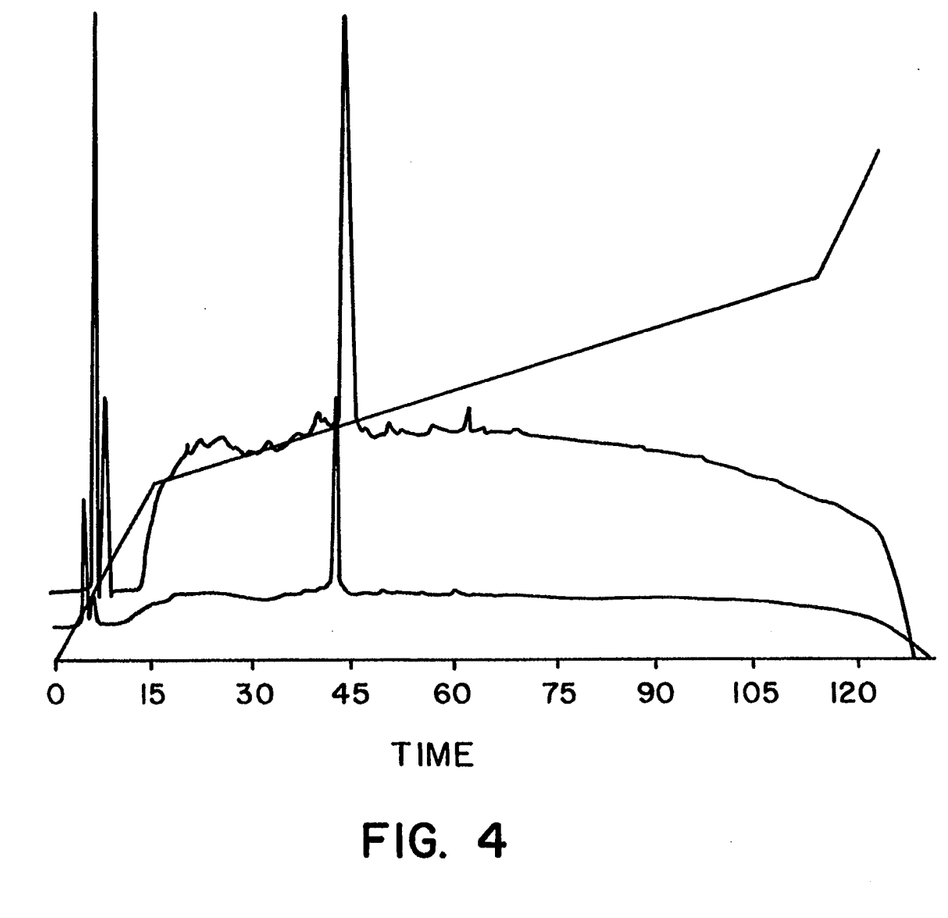

The chromatographic behavior of the $glu^{3,5}$hbFGF the presence and absence of dithiothreitol on heparin and RP-HPLC is similar to that observed for native sequence hbFGF. The cysteine to serine mutation greatly facilitates the purification of this analogue since it behaves as a single species on heparin- and $C_4$ RP-HPLC (FIG. 4) and thus eliminates the need for dithiothreitol treatment during purification.

(b) Sequence Analyses

N-terminal sequence analyses of reverse phase purified proteins are performed on a model 477A pulsed-liquid phase sequencer (from Applied Biosystems, CA) equipped with an on-line phenylthiohydantoin- amino acid analyzer (Model 120A, Applied Biosystems, California). Amino acid compositions are determined after HCl gas phase hydrolysis (5.7M HCl/0.1% phenol; 24 h at 110° C.) using a model 420A phenylisothiocyanate-derivatizer equipped with an on-line model 130A separation system (Applied Biosystems, California).

N-terminal sequence analysis of the material isolated from heparin HPLC gives a single sequence consistent with $glu^{3,5}$hbFGF (2-155) indicating complete removal of the N-terminal methionine.

(c) Molecular Weights

Molecular weight determinations are performed on a 10 to 15% gradient and 20% homogeneous polyacrylamide gels in the presence of sodium dodecyl sulfate (SDS-PAGE) using a silver stain detection system (Phastgel System, Pharmacia/LKB).

hbFGF (2-155) migrates with an $M_r$ of 17,000 compared to an $M_r$ value of about 19,000 for $glu^{3,5}$hbFGF. Molecular weights calculated from amino acid sequence data for hbFGF and the chimeric version are 17,124 and 17,224, respectively. To resolve the apparent molecular weight discrepancy, a sample of $glu^{3,5}$hbFGF is analyzed by liquid-secondary ion mass spectrometry and gives a molecular ion of mass 17,365. This value is, within experimental error, consistent with that predicted from sequence data. While not wishing to be bound to any theory, the anomalous migration of $glu^{3,5}$ on polyacrylamide gels under denaturing conditions is most likely due to interference of protein-SDS interactions from the glutamyl side chains at positions 3 and 5.

On SDS-PAGE $glu^{3,5}, ser^{78,96}$hbFGF also migrates as an $M_r$ 19,000 protein and not as a predicted $M_r$ 17,000 species. This observation is consistent with the aberrant migration noted for $glu^{3,5}$hbFGF.

EXAMPLE 7

Bioassay of Native and Mutant hbFGF Derivatives

The mitogenic activity of native sequence hbFGF and mutants is determined using bovine vascular endothelial cells derived from adult aortic arch as described by Esch, et al., Proc. Nat. Acad. Sci. USA 82: 6507-6511 (1985). Cells are seeded at the initial density of $0.8 \times 10^4$ cells per 24-well plate in 0.5 ml Dulbecco's modified Eagle's medium (DMEM) containing 10% calf serum (Hyclone, Logan, Utah) supplemented with penicillin (100 units/ml), streptomycin (100 µg/ml) and L-glutamine (2 mM). Two hours after plating, 20 µl-aliquots of appropriate dilutions (0.001 to 100 ng/ml) of bFGF in DMEM containing 0.5% bovine serum albumin (BSA) are added. After 5 days in culture, duplicate plates are trypsinized and cell densities determined by cell counting in a Coulter counter.

Alternatively, growth curves in the presence and absence of bFGF are determined by measuring acid phosphatase levels after cell lysis using p-nitrophenyl phosphate as substrate (Connolly, D. T., et al., Anal. Biochem. 152:136–140 (1986), page 137). Cells are seeded at an initial cell density of 1000 to 1200 cells per well (0.32 cm$^2$, 0.64 cm diameter flat bottomed 96 well plates) in 0.25 ml DMEM containing 10% calf serum, antibiotics and L-glutamine. After plating, 10 µl-aliquots of appropriate dilutions of growth factor (0,001 to 100 ng/ml) in DMEM containing 0.5% BSA are added.

After 4 to 5 days in culture, each well is washed and 100 µl pH 5.5 buffer containing 0.1M sodium acetate, 0.1% Triton X-100 and 10 mM p-nitrophenyl phosphate (Sigma 104 phosphatase substrate) are added to each well. The plates are incubated at 37° C. for 2 hours, the reaction stopped by adding 10 µl of 1N sodium hydroxide, and color development determined at 405 nm against a buffer blank incubated without cells using a UV max kinetic microplate reader (Molecular Devices, California). Determinations are made in triplicate. Both methods give indistinguishable dose-response curves.

When the mitogenic properties of recombinant hbFGF and mutant proteins are compared to those of bFGF (10–155) originally isolated from bovine brain, human recombinant bFGF and $glu^{3,5}$hbFGF show a dose-dependent stimulation of endothelial cell growth that is essentially identical to that for bovine brain bFGF (FIG. 5) and exhibit doses for half-maximal stimulation (median effective dose, ED$_{50}$) of 0.3 to 1.0 ng/ml and a maximal stimulation between 3 and 10 ng/ml. Replacement of cysteine 78 and 96 with serine to give $glu^{3,5}, ser^{78,96}$hbFGF has no effect on the mitogenic potency and gives a dose-response curve that is indistinguishable from that determined for tissue-derived bovine bFGF (FIG. 6).

The above description is for the purpose of teaching the person of ordinary skill in the art how to practice the present invention and it is not intended to detail all those obvious modifications and variations of it which will become apparent to the skilled worker upon reading the description. It is intended, however, that all such obvious modifications and variations be included within the scope of the present invention as defined in the appended claims.

The DNA sequences, plasmids and/or microorganisms deposited in connection with the present patent application, except where specified to the contrary, are deposited in American Cyanamid Company's culture collection maintained in Pearl River, N.Y. and are available to the public when legally appropriate to do so. Further, the following are deposited additionally with the American Type Culture Collection (ATCC) in Rockville, Md. 20952, U.S.A. on the date indicated with the ATCC accession numbers indicated:

BL21 lysS/pET glu$^3$, $^5$ser$^{78, 96}$ deposited on Nov. 13, 1990 with ATCC No. 68478

BL21 lys-S/pET glu$^3$, $^5$hbFGF deposited on Nov. 13, 1990 with ATCC No. 68477.

The above two contain the DNA of glu$^3$, $^5$ser$^{78, 96}$hbFGF and glu$^3$, $^5$hbFGF as described herein.

BIBLIOGRAPHY

1. Abraham, J. A., et al., EMBO J. 5: 2523–2528 (1986).
2. Arakawa, T. and Fox G. M., Eur. Pat. Ap. No. 320,148 (1989).
3. Barr, P. J., et al., Biol. chem. 263: 16471–16478 (1988).
4. Bergonzoni, L., et al., Eur. Pat. Ap. Pub. No. 363,675 (1989).
5. Burgess, W. H., and Maciag, T., Ann. Rev. Biochemo 8: 575–606 (1989).
6. Connolly, D. T., et al., Anal. Biochem. 152: 136–140 (1986).
7. Davidson, J. M., et al., J. Cell Bio. 100: 1219–1227 (1985).
8. Esch, F., et al., Proc. Nat. Acad. Sci. USA 82: 6507–6511 (1985).
9. Esch, F., et al., Eur. Pat. Ap. Pub. 228,449 (1986).
10. Fiddes, J. C., et al., Eur. Pat. Ap. Pub. No. 298,723 (1989).
11. Franco, W. P., U.S. Pat. No. 4,296,100 (1981).
12. Franco, W. P., U.S. Pat. No. 4,378,347 (1983).
13. Gospodarowicz. D., Nature 249:123–127 (1974).
14. Gospodarowicz. D., et al., Nat. Cancer Insfl. Mon. 48: 109–130 (1978).
15. Gospodarowicz, D., et al., Proc. Nat. Acad. Sci. USA 81: 6963–6967 (1984).
16. Gospodarowicz, D. et al., U. S. Pat No. 4,785,079 (1988).
17. Gospodarowicz. D. et al., U.S. Pat No. 4,902,782 (1990).
18. Iwane, M., et al., Biochem. Biophys. Res. Commun. 146: 470–477 (1987).
19. Rosenberg, A., et al., Gene 56: 125–135 (1987).
20. Sanger, F., et al., Proc Nat. Acad. Sci. 74: 5463–5467 (1977).
21. Seno, M., et al., Eur. Pat. Ap. Publ. No. 281,822 (1988).
22. Seno, M., et al., Eur. Pat. Ap. Pub. No. 326,907 (1989).
23. Squires, C. H., et al., J. Biol. Chem. 263: 16297–16302 (1988).
24. Thomas Jnr. K. A. and Linemeyer, D. L., Eur. Pat. Ap. Pub. No. 319,052 (1989).
25. Walicke, P., et al., Proc. Nat. acad. Sci. USA 83: 3012–3016 (1986).

---

What is claimed is:

1. A DNA sequence selected from the group consisting of:
   (a) DNA sequences that code for a recombinant human fibroblast growth factor having about 155 amino acids wherein the alanine at position 3 and the serine at position 5 are replaced with glutamic acid; and
   (b) DNA sequences that code for a recombinant human fibroblast growth factor having about 155 amino acids wherein the alanine at position 3 and the serine at position 5 are replaced with glutamic acid, and the cysteines at positions 78 and 96 are replaced with amino acids that eliminate disulfide scrambling.

2. A biologically functional circular plasmid or viral DNA vector comprising the DNA sequence according to claim 1.

3. The vector according to claim 2 wherein said vector is a pET-3a derivative selected from the group consisting of pT7 Kan 5 containing the T7 promoter for RNA polymerase and pET-3a(m13).

4. An *E. coli* cell transformed with the DNA encoded in the vector according to claim 2 in a manner allowing said *E. coli* cell to express fibroblast growth factor.

5. A procaryotic or eucaryotic host cell transformed or transfected with the DNA sequence according to claim 1 in a manner allowing the host cell to express a fibroblast growth factor.

6. A biologically functional circular plasmid or viral DNA vector comprising a DNA sequence encoding a recombinant chimeric basic fibroblast growth factor selected from the group consisting of:
   (a) a chimeric basic fibroblast growth factor having about 155 amino acids wherein the alanine at position 3 and the serine at position 5 are replaced with glutamic acid;
   (b) a chimeric basic fibroblast growth factor having about 155 amino acids wherein the alanine at position 3 and the serine at position 5 are replaced with glutamic acid, and the cysteines at positions 78 and 96 are replaced with amino acids that eliminate disulfide scrambling; and
   (c) (a) or (b) having no N-terminal methionine.

7. The vector according to claim 6 comprising a pET-3a derivative.

8. The vector according to claim 7 selected from the group consisting of pT7 Kan 5 containing the T7 promoter from RNA polymerase and pET-3a(M13).

9. A procaryotic or eucaryotic host cell transformed or transfected with the vector of claim 6 in a manner allowing the host cell to express said factor.

10. The cell according to claim 9 comprising *E. coli*.

11. A method for producing a recombinant chimeric human basic fibroblast growth factor selected from the group consisting of:
   (a) a chimeric basic fibroblast growth factor having about 155 amino acids wherein the alanine at position 3 and the serine at position 5 are replaced with glutamic acid;
   (b) a chimeric basic fibroblast growth factor having about 155 amino acids wherein the alanine at position 3 and the serine at position 5 are replaced with glutamic acid, and the cysteines at positions 78 and 96 are replaced with amino acids that eliminate disulfide scrambling; and
   (c) (a) or (b) having no N-terminal methionine, said method comprising propagating host cells transformed or transfected with a purified and isolated DNA sequence coding for the fibroblast growth factor in culture medium for a time and under conditions sufficient for said host cells to express said growth factor, and therefrom recovering growth factor from materials selected from the group consisting of said culture medium, lysates of said host cells and membrane fractions of said host cells.

12. The method according to claim 11, wherein said host cells are *E. coli* cells.

13. The method according to claim 12 wherein said fibroblast growth factor is selected from the group consisting of $glu^{3,5}hbFGF$ and $glu^{3,5},ser^{78,96}hbFGF$.

14. A method for producing procaryotic or eucaryotic cells capable of expressing a recombinant chimeric human basic fibroblast growth factor selected from the group consisting of:
   (a) a chimeric basic fibroblast growth factor having about 155 amino acids wherein the alanine at position 3 and the serine at position 5 are replaced with glutamic acid;
   (b) a chimeric basic fibroblast growth factor having about 155 amino acids wherein the alanine at position 3 and the serine at position 5 are replaced with glutamic acid and the cysteines at positions 78 and 96 are replaced with amino acids that eliminate disulfide scrambling; and (c) (a) or (b) having no N-terminal methionine, said method comprising transfecting or transforming procaryotic or eucaryotic host cells with a DNA sequence encoding for the fibroblast growth factor in a manner allowing said host cells to express the polypeptide encoded by said DNA.

15. The method according to claim 14 wherein said cells are *E. coli* cells.

16. The method according to claim 15 wherein said fibroblast growth factor is selected from the group consisting of glu$^{3,5}$hbFGF and glu$^{3,5}$,ser$^{78,96}$hbFGF.

* * * * *